United States Patent [19]

Hino et al.

[11] Patent Number: 4,668,712
[45] Date of Patent: May 26, 1987

[54] PHOTOPOLYMERIZABLE COMPOSITION

[75] Inventors: Kenichi Hino; Junichi Yamauchi; Koji Nishida, all of Kurashiki, Japan

[73] Assignee: Kuraray Co., Ltd., Kurashiki, Japan

[21] Appl. No.: 689,302

[22] Filed: Jan. 7, 1985

[30] Foreign Application Priority Data

Jan. 17, 1984 [JP] Japan .................................. 59-6797

[51] Int. Cl.$^4$ ........................... C08F 2/50; C08F 4/34; C08F 4/40; C08L 63/10
[52] U.S. Cl. ......................................... 522/13; 522/19; 522/24; 522/96; 522/103; 522/92; 523/116
[58] Field of Search ..................... 204/159.23; 522/13, 522/19, 24

[56] References Cited

U.S. PATENT DOCUMENTS

| | | | |
|---|---|---|---|
| 3,368,900 | 2/1968 | Burg | 430/288 |
| 3,756,827 | 9/1973 | Chang | 96/86 P |
| 4,071,424 | 1/1978 | Dart | 204/159.15 |
| 4,459,193 | 7/1984 | Ratcliffe | 204/159.23 |

FOREIGN PATENT DOCUMENTS 54-130693 3/1978 Japan .
56-120610 2/1980 Japan .

OTHER PUBLICATIONS

Bjorksten, "Polyesters and Their Applications", Reinhold, 1956—pp. 52–61.
Murayama, "Intermediates in the Photochemical Reactions of Camphorquinone with Aliphatic Aldehydes", Chemistry Letters (1974) pp. 467–470.

*Primary Examiner*—John C. Bleutge
*Assistant Examiner*—Arthur H. Koeckert
*Attorney, Agent, or Firm*—Oblon, Fisher, Spivak, McClelland & Maier

[57] ABSTRACT

A photopolymerizable composition composed of a polymerizable monomer and an initiator capable of polymerizing said monomer upon exposure to visible light, characterized in that said initiator consists essentially of (a) at least one kind of photosensitizer selected from an $\alpha$-diketone, quinone, and derivatives thereof, and (b) at least one kind of accelerator selected from an aldehyde containing no amino groups and derivatives thereof.

10 Claims, No Drawings

PHOTOPOLYMERIZABLE COMPOSITION

BACKGROUND OF THE INVENTION

1. Field of the Invention

The present invention relates to a photopolymerizable composition which polymerizes and cures upon exposure to visible light on account of a new polymerization initiator contained therein. More particularly, it relates to a photopolymerizable composition suitable for use in dental applications.

2. Description of the Prior Art

Recently, photopolymerizable resins which cure upon exposure to ultraviolet rays and visible light are replacing thermosetting resins which cure upon heating in many application areas such as paints, printing inks, adhesives, coating materials, and dental filling materials.

Heretofore, the photopolymerizable dental composite resin has been of UV curable type or visible light curable type. The one of UV curable type has a disadvantage that curing by irradiation does not reach as deep as required, and a part of it remains uncured at the innermost recess of the tooth cavity. It has another disadvantage of being poor in adhesion to the tooth. These disadvantages have been overcome to some extent with the advent of visible light curable composite resin. Nevertheless, it does not cure completely when a deep tooth cavity is filled by a single application, and filling has to be done twice. It is considered that these drawbacks are attributable to the insufficient curing performance of the photopolymerization initiator.

The conventional polymerization initiators for photopolymerizable compositions are disclosed in U.S. Pat. Nos. 4,071,424 and 4,459,193. The former discloses the use of $\alpha$-diketone and amine as the photosensitizer and accelerator, and the latter teaches the combined use of fluorenone or $\alpha$-diketone and an organic peroxide and optionally an amine. These conventional polymerization initiators have some disadvantages. That is, the $\alpha$-diketone/amine type and the fluorenone/or $\alpha$-diketone/organic peroxide type are not sufficient in curing rate and cure depth, and consequently they are not of practical use. On the other hand, the fluorenone/or $\alpha$-diketone/organic peroxide/amine type has a high curing rate but is so poor in storage stability that it cannot be packed together with a resin composition. The poor storage stability may be overcome by packing amine separately from $\alpha$-diketone/or fluorenone/peroxide. The separate packs are combined together just before use. But this is troublesome and undesirable.

Japanese Patent Laid-open No. 130693/1979 discloses a UV polymerization initiator composed of benzil and N,N-dialkylaminobenzaldehyde. This one is not of practical use either because of its poor storage stability and its tendency toward discoloring the cured product.

SUMMARY OF THE INVENTION

Accordingly, it is an object of this invention to provide a photopolymerizable composition containing a photopolymerization initiator which cures at a high rate and cures to a sufficient depth and hardly discolors and has good storage stability.

It is another object of this invention to provide a method for restoring tooth cavities with a photopolymerizable composition containing a photopolymerization initiator which cures at a high rate and cures to a sufficient depth.

The other objects of this invention will be apparent from the description that follows.

These objects are achieved by this invention which provides a photopolymerizable composition composed of a polymerizable monomer and an initiator capable of polymerizing said monomer upon exposure to visible light, characterized in that said initiator consists essentially of (a) at least one kind of photosensitizer selected from $\alpha$-diketone, quinone, and derivatives thereof, and (b) at least one kind of accelerator selected from an aldehyde containing no amino groups and derivatives thereof.

DETAILED DESCRIPTION OF THE INVENTION

According to this invention, the polymerizable monomer is properly selected depending on the object and application; and it is usually (meth)acrylic ester for dental use. Other preferred examples include esters of $\alpha$-cyanoacrylic acid, crotonic acid, cinnamic acid, sorbic acid, maleic acid, and itaconic acid with a mono- or dihydric alcohol; (meth)acrylamides such as N-isobutylacrylamide; carboxylic vinyl esters such as vinyl acetate; vinyl ethers such as butyl vinyl ether; and mono-N-vinyl compounds such as N-vinyl-2-pyrolidone; and styrene or derivatives thereof.

Preferred examples of the (meth)acrylic ester are mono and polyfunctional ones and urethane (meth)acrylate as listed below.

(i) Monofunctional:

Methyl (meth)acrylate, n- or i-propyl (meth)acrylate, n-, i-, or t-butyl (meth)acrylate, 2-hydroxyethyl methacrylate, etc.

(ii) Difunctional:

Di(meth)acrylate of ethylene glycol, diethylene glycol, triethylene glycol, tetraethylene glycol, dodecaethylene glycol, tetradecaethylene glycol, etc. represented by the formula below.

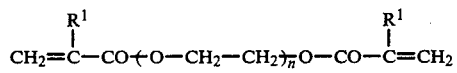

(where n is an integer of 1 to 14, and $R^1$ is hydrogen or a methyl group). Glycerin di(meth)acrylate, 2,2'-bis[p-($\gamma$-methacryloxy-$\beta$-hydroxypropoxy)phenyl]propane, bisphenol A dimethacrylate, neopentylglycol di(meth)acrylate, 2,2'-di(4-methacryloxy-polyethoxyphenyl)propane (with 2 to 10 ethoxy groups in one molecule), 1,2-bis(3-methacryloxy-2-hydroxypropoxy)-butane, etc.

(iii) Tri- or polyfunctional:

Trimethylolpropane tri(meth)acrylate, pentaerythritol tetra(meth)acrylate, etc.

(iv) Urethane (meth)acrylate:

Reaction products of 2 mol of (meth)acrylate monomer having hydroxyl groups and 1 mol of diisocyanate; and reaction products of a urethane prepolymer with terminal NCO groups and a (meth)acrylate monomer having hydroxy groups. The reaction product has the formula below.

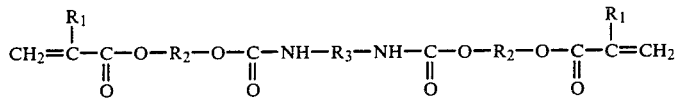

(where $R_1$ is hydrogen or a methyl group, $R_2$ is an alkylene group, and $R_3$ is an organic residue.) Examples include a reaction product of 2,2,4-trimethylhexamethylene diisocyanate and oxypropyl methacrylate as disclosed in Japanese Patent Publication No. 36960/1976; and a reaction product of a urethane prepolymer having terminal isocyanate groups and 2-oxyethyl methacrylate as disclosed in Japanese Patent Publication No. 33687/1980. Another monomer that can be used in this invention is tetrafunctional one as disclosed in U.S. Pat. No. 4,386,912 (See Example 3 mentioned later).

In addition to the above-mentioned monomers, it is possible to use a polymerizable monomer having an acid group which is capable of bonding to teeth and metal and other adherends. Usually, such a monomer is used in a small amount in combination with the above-mentioned monomer. Examples of such monomers include those which contain carboxyl groups (or anhydride thereof) of (meth)acrylic acid, maleic anhydride, crotonic acid, or 4-(meth)acryloxyethyltrimellitic acid; di(meth)acryloxyglycerophosphoric acid, (meth)acryloxyethylphosphoric acid, or glyceroldi(meth)acrylate monofluorophosphate; and those which contain phosphoric acid group or phosphoric chloride group as disclosed in U.S. Pat. Nos. 4,259,075, 4,259,117, and 4,368,043; European Patent Application Publication Nos. 74,708 and 58,483; and Japanese Patent Laid-open No. 164171/1982.

The photosensitizer used in this invention is at least one kind selected from α-diketone, quinone, and derivatives thereof, which gives a UV and visible spectrum with apparent absorption at 380 to 500 nm. These photosensitizers are represented by the following formulas.

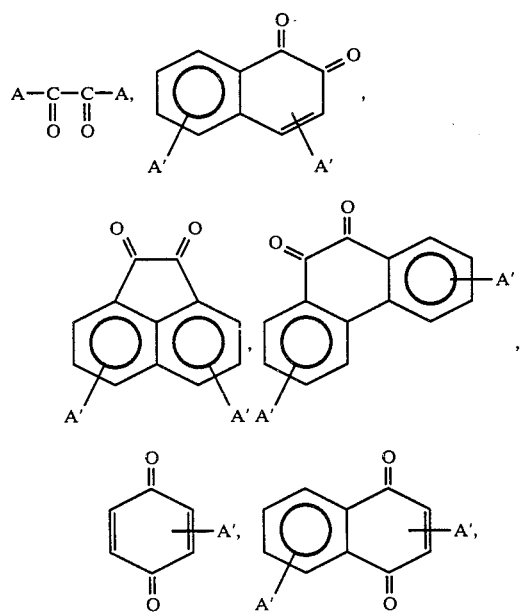

-continued

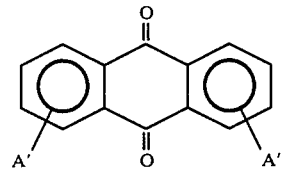

(where A denotes an aliphatic hydrocarbon group of 1 to 20 carbon atoms, two of A may be the same or different, and two of A may bond to each other to form a cyclic structure; and A' denotes 2 to 4 hydrogen atoms or an aliphatic hydrocarbon group or groups having 1 to 20 carbon atoms, two of A' may be the same or different.)

Examples of these photosensitizers include acyclic α-diketone compounds such as diacetyl, 2,3-pentanedione, 2,3- or 3,4-hexanedione, and 2,3-, 3,4-, or 4,5-octanedione; alicyclic α-diketone compounds such as camphorquinone (common name of 1,7,7-trimethylbicyclo[2.2.1]heptane-2,3-dione) and bicyclo[2.2.1]heptane-2,3-dione; polynuclear quinones such as 9,10-phenanthrenequinone, 9,10-anthraquinone, acenaphthenequinone, and α- or β-naphthoquinone; and alkyl derivatives of polynuclear quinones such as 2-methyl-1,4-naphthoquinone, 2-t-butyl-9,10-anthraquinone, and 2-ethylanthraquinone.

Preferable among them are camphorquinone, phenanthraquinone, acenaphthenequinone, β-naphthoquinone, anthraquinone, 2,3-pentanedione, and 2,3-, 3,4-, and 4,5-octanedione. The photosensitizer is used in concentration of 0.01 to 5 wt% based on the quantity of the polymerizable monomer.

The aldehyde or derivative thereof which is used as the accelerator in this invention should preferably be a compound represented by the formula $B(CHO)_n$ (where B denotes an acyclic or alicyclic saturated or unsaturated aliphatic hydrocarbon group having 1 to 20 carbon atoms or a monocyclic or polycyclic aromatic hydrocarbon group of 1 to 20 carbon atoms; the hydrogen group may have a substituent group of 1 to 20 carbon atoms; examples of the substituent group include alkyl group, polyalkyl ether group, alkenyl group, cycloalkyl group, aryl group, alkylaryl group, arylalkyl group, acyl group, hydroxyl group, carboxyl group, alkoxycarbonyl group, alkoxy group, phenoxy group, halogeno group, cyano group, cycanomethyl group, alkylthio group, thiol group, carbamoyl group, and alkylamide group; and n is an integer of 1 to 3.) Preferred compounds are alkylmonoaldehyde or alkyldialdehyde of 1 to 20 carbon atoms; polyalkyl ether mono- or dialdehyde of 1 to 20 carbon atoms; and the one represented by formula

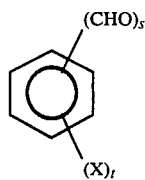

(where s is 1 or 2; X denotes an alkyl, alkoxy, or polyalkylether of 1 to 20 carbon atoms; and t is an integer of 0 to 3)

Examples of such aldehyde compounds include valeraldehyde, 2-ethylhexylaldehyde, decylaldehyde, tetradecylaldehyde, octadecylaldehyde, citral, citronellal, farnesal, tetrahydrocitral, hexahydrofarnesal, hexahydrobenzaldehyde, phenylacetoaldehyde, 2-(p-t-butylbenzyl)propionaldehyde, aldol, hydroxycitronellal, glutaric dialdehyde, 1,9-nonanedial,

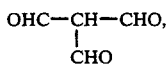

2-methoxyethoxyacetaldehyde (CH$_3$—O—CH$_2$CH$_2$—O—CH$_2$CHO), 2-(2-methoxyethoxy)ethoxyacetaldehyde (CH$_3$O—CH$_2$CH$_2$O—CH$_2$CH$_2$O—CH$_2$CHO), p-[2-(2-methoxyethoxy)ethoxy]benzaldehyde

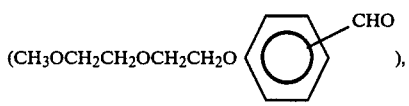

2-(2-methoxyethoxy)ethylbenzaldehyde

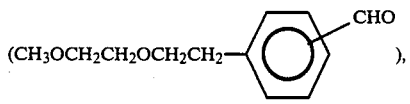

benzaldehyde, (o,m,p)-tolualdehyde, (o,m,p)-octylbenzaldehyde, (o,m,p)-anisaldehyde, (o,m,p)-butylocybenzaldehyde, (o,m,p)-octyloxybenzaldehyde, 3,4-diethoxybenzaldehyde, 3,4,5-trimethoxybenzaldehyde, (o,m,p)-phthalicdicarboaldehyde, (o,m,p)-hydroxybenzaldehyde, (o,m,p)-phenylbenzaldehyde, (o,m,p)-phenoxybenzaldehyde, (o,m,p)-cyanobenzaldehyde, (o,m,p)-chlorobenzaldehyde, 2,4-dichlorobenzaldehyde,

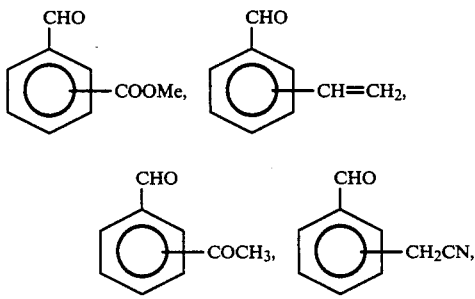

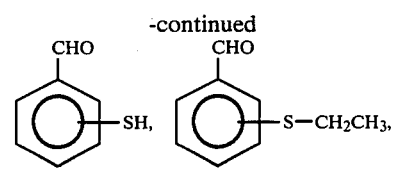

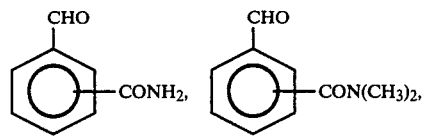

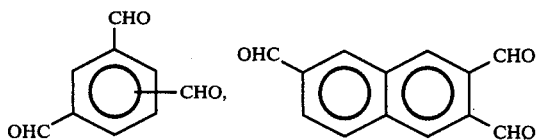

2-naphthoaldehyde, 1,2,3,4-tetrahydro-2-naphthaldehyde, Δ$^3$-tetrahydrobenzaldehyde, 3,6-dioxaoctane-1,8-dial. Those which have a weak smell or pleasant odor are of practical use.

Those compounds which are not preferable in this invention are low-molecular weight (lower than 80) aliphatic aldehydes such as acetaldehyde and butanal, which are ill-smelling and flammable. Those aldehdyes having an amino group are not used either in this invention, because they are unstable. Although dialkylaminobenzaldehyde, is exceptionally stable, it is not suitable in this invention because it discolors the cured resin composition when used in combination with an α-diketone.

The above-mentioned aldehyde is used in concentration of 0.1 to 10 wt% based on the quantity of the polymerizable monomer.

In order to increase the curing rate in this invention, it is desirable to add an organic peroxide to the photosensitizer and accelerator. In the case of conventional photopolymerization initiator composed of α-diketone and amine, the addition of organic peroxide extremely decreases the storage stability due to the amine-peroxide redox reaction. In contrast, the photopolymerization initiator in this invention permits the combined used of organic peroxide, ensuring storage stability longer than one year. This invention provides a photopolymerization initiator which is superior in both curing rate and storage stability. Such performance has never been expected from the prior art.

Examples of the organic peroxide used in this invention include diacyl peroxides and peroxyesters. Preferable among them are benzoyl peroxide, t-butyl perbenzoate, di-t-butyl diperoxyisophthalate, 2,5-dimethyl-2,5-di(benzoylperoxy)-hexane, and other peroxides in the form of derivatives of benzoic acid. The peroxide is used in concentration of 0.1 to 10 wt% based on the quantity of the polymerizable monomer.

The composition of this invention may be used, in addition to the above-mentioned polymerizable monomer and photopolymerization initiator, with various kinds of organic or inorganic fillers. Organic fillers include polymethyl(meth)acrylate and polyethyl(meth)acrylate and polymer-coated inorganic fillers. Inorganic fillers include silicon dioxide, alumina, glass ceramics, diatomaceous earth, kaolin, montmorillonite, clay, Japanese acid clay, synthetic zeolite, mica, calcium fluoride, calcium phosphate, barium sulfate, zirconium dioxide, titanium dioxide, etc. in the form of powder, fiber, or flake. In the case where the composition of this invention is used in dental application, the inorganic filler should usually be treated with γ-methacryloxypropopylterimethoxysilane, vinyltrichlorosilane, vinyltriethoxysilane, vinyltrimethoxysilane, vinyltriacetoxysilane, vinyltri(methoxyethoxy)silane, and other silane compounds. The surface treatment may be accomplished in the usual way.

In the case where the composition of the invention is used as a dental filling compound as mentioned later, the filler should be added in an amount of 20 to 90 wt%, preferably 50 to 85 wt%, based on the composition, and the quantity of the poymerizable monomer should be 80 to 10 wt%, preferably 50 to 15 wt%, based on the composition.

Moreover, the composition of this invention may be incorporated with a polymerization inhibitor, coloring agent, UV absorber, and other additives, as required.

The above-mentioned components are usually mixed into paste or liquid by the manufacturer, and it is delivered to the user in one or two light-shielding containers. The user will apply the composition to a substrate and cures it in the usual way by irradiating with visible light.

As mentioned above, the composition of this invention contains a specific photopolymerization initiator, cures at a high rate, and has good storage stability. The cured product thereof is not discolored. Thus, it greatly out-performs the conventional photopolymerizable composition.

The composition of the invention will find use as dental restorative materials, paints, printing inks, adhesives, films, and other coating materials. It is particularly useful as a dental composite filling material for filling and restoring tooth cavities. In addition, it will find use as a dental crowns material, artificial teeth material, dental adhesive, dental cementing material, and filling material for preventing caries.

In the case where the composition of this invention is used as a dental composite filling material, it is incorporated with a filler. Prior to filling, the tooth cavity is etched with an aqueous solution of phosphoric acid and then treated with a bonding agent containing acidic monomer. After filling, the composition is irradiated with visible light for curing.

The invention is now described with reference to the following examples, which should not be construed to restrict the scope of the invention.

EXAMPLE 1

A monomer liquid was prepared from 70 parts by weight of 2,2-bis[4-(3-methacryloyloxy-2-hydroxypropoxy)phenyl]-propane (referred to as bis-GMA hereinafter), 15 parts by weight of triethyleneglycol dimethacrylate (referred to as 3G hereinafter), and 15 parts by weight of neopentylglycol dimethacrylate (referred to as NPG hereinafter). This monomer liquid was incorporated with 1 wt% of camphorquinone and an aldehyde as shown in Table 1 to give the composition of the invention. The resulting composition was placed in a cylindrical glass container (1 ml in capacity and 10 mm in diameter) and irradiated with visible light to examine the curing time. The light source was a slide projector (Model HILUX-H130, made by Rikagaku Seiki Co., Ltd.) equipped with a halogen-tungsten lamp (1 kW). Two cutoff filters (2E filter of Eastman Kodak Company) were placed on the lens to remove ultraviolet rays (415 nm). The glass container was placed 20 cm away from the lens and the light was directed upward to the bottom of the container. The results are shown in Table 1-1.

TABLE 1-1

| No. | Aldehyde | Amount (mg) | Monomer* liquid (mg) | Curing time (sec) |
|---|---|---|---|---|
| 1 | Control | — | 226.0 | 240 |
| 2 | p-Tolualdehyde | 4.5 | 239.8 | 37 |
| 3 | p-n-Octylbenzaldehyde | 5.2 | 220.7 | 41 |
| 4 | p-Anisaldehyde | 4.4 | 235.4 | 42 |
| 5 | p-n-Hexyloxybenzaldehyde | 5.0 | 225.3 | 43 |
| 6 | o-Phthalaldehyde | 3.7 | 246.7 | 38 |
| 7 | Benzaldehyde | 3.7 | 233.5 | 45 |
| 8 | Lauraldehyde | 3.8 | 222.8 | 27 |
| 9 | Citronellal | 2.6 | 232.5 | 25 |
| 10 | 1,9-Nonanedial | 3.2 | 207.1 | 24 |
| 11 | Glutaric dialdehyde** | 6.0 | 231.5 | 35 |

*Monomer liquid contains camphorquinone.
**40% aqueous solution.

COMPARATIVE EXAMPLE 1

Compositions were prepared by incorporating the monomer liquid obtained in Example 1 with 1 wt% of camphorquinone and various amines as shown in Table 1-2. The curing time was measured in the same way as in Example 1. The results are shown in Table 1-2.

TABLE 1-2

| No. | Amine | Amount (mg) | Monomer* liquid (mg) | Curing time (sec) |
|---|---|---|---|---|
| 1 | N,N—dimethylaminoethyl methacrylate | 5.1 | 295.0 | 55 |
| 2 | Triethylamine | 4.7 | 230.1 | 90 |
| 3 | N,N—dimethylethanolamine | 4.1 | 221.7 | 110 |
| 4 | n-Butylamine | 4.0 | 247.6 | 110 |
| 5 | N,N—diethanol-p-toluidine | 5.0 | 230.3 | 120 |

*Monomer liquid contains camphorquinone.

EXAMPLE 2

Compositions were prepared by incorporating the monomer liquid obtained in Example 1 with camphorquinone (1 wt%), tolualdehyde (1.1 wt%), and various organic peroxides as shown in Table 2. The curing time was measured in the same way as in Example 1. The results are shown in Table 2.

TABLE 2

| No. | Peroxide | Amount (mg) | Monomer* liquid (mg) | Curing time (sec) |
|---|---|---|---|---|
| 1 | Control | — | 233.0 | 47 |
| 2 | Benzoyl peroxide | 2.3 | 246.0 | 30 |
| 3 | t-Butylperbenzoate | 5.5 | 220.8 | 33 |
| 4 | di-t-Butylperoxyisophthalate | 4.6 | 227.2 | 32 |
| 5 | 2,5-dimethyl-2,5-di(benzoilperoxy)hexane | 2.3 | 218.5 | 29 |

*Monomer liquid contains camphorquinone and tolualdehyde.

EXAMPLE 3 AND COMPARATIVE EXAMPLE 2

A monomer liquid composed of 50 parts by weight of U-4TH (urethane tetramethacrylate monomer having the formula below) and 50 parts by weight of 3G was incorporated with 0.23 wt% of acenaphthenequinone.

U-4TH

-continued

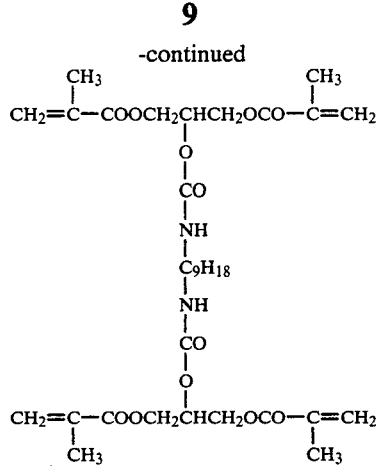

The resulting solution was incorporated with p-tolualdehyde and peroxide A (t-butylperbenzoate) or peroxide B (2,5-dimethyl-2,5-di(benzoylperoxy)hexane) as shown in Table 3. The resulting compositions were examined for curing time in the same way as in Example 1. The results are shown in Table 3. The compositions for comparison were not incorporated with p-tolualdehyde.

TABLE 3

| No. | Monomer liquid containing acenaphthenequinone (mg) | Amount of p-tolualdehyde added (mg) | Peroxide and amount added (mg) | Curing time (sec) |
| --- | --- | --- | --- | --- |
| 1* | 218.4 | — | — | 125 |
| 1 | 219.7 | 1.5 | — | 75 |
| 2* | 214.2 | — | A 5.1 | 115 |
| 2 | 235.4 | 3.7 | A 5.5 | 62 |
| 3* | 214.2 | — | B 4.3 | 110 |
| 3 | 233.0 | 3.4 | B 4.7 | 58 |

*Comparative examples.

EXAMPLE 4 AND COMPARATIVE EXAMPLE 3

A monomer liquid composed of 33 parts by weight of U-4TH, 33 parts by weight of 2,2'-di(4-methacryloxypolyethoxyphenyl)propane (having 2 to 3 (2.6 on average) ethoxy groups in one molecule), and 33 parts by weight of 3 G was incorporated with 0.95 wt% of camphorquinone. The monomer solution was made into compositions by adding t-butyl perbenzoate and lauraldehyde as shown in Table 4. The resulting compositions were examined for curing time in the same way as in Example 1. The compositions for comparison were not incorporated with lauraldehyde. The results are shown in Table 4.

TABLE 4

| No. | Monomer liquid containing camphorquinone (mg) | Amount of lauraldehyde added (mg) | t-Butyl perbenzoate added (mg) | Curing time (sec) |
| --- | --- | --- | --- | --- |
| 1* | 252.0 | — | — | 140–150 |
| 1 | 242.6 | 1.9 | — | 46 |
| 2* | 240.9 | — | 9.0 | 80 |
| 2 | 240.8 | 1.8 | 8.6 | 31 |

*Comparative examples.

EXAMPLE 5 AND COMPARATIVE EXAMPLE 4

The same monomer liquid as in Example 1 was incorporated with 0.05 wt% of phenanthraquinone, 0.32 wt% of benzoyl peroxide, and citronellal as shown in Table 5. Compositions for comparison were not incorporated with citronellal. The resulting compositions were examined for curing time. The same experiments were also carried out on compositions in which the monomer liquid was incorporated with 1.0 wt% of anthraquinone and 1.38 wt% of benzoyl peroxide. The results are shown in Table 5.

TABLE 5

| No. | Monomer liquid containing quinone & BPO* (mg) | Amount of citronellal added (mg) | Curing time (sec) |
| --- | --- | --- | --- |
| 1** | 222.0 | — | 43 (comparative) |
| 1** | 219.3 | 3.7 | 28 |
| 2*** | 225.3 | — | 150 (comparative) |
| 2*** | 220.1 | 5.0 | 90 |

*BPO: benzoyl peroxide
**with phenanthraquinone
***with anthraquinone

EXAMPLE 6

The same monomer liquid as prepared in Example 1 was incorporated with 0.97 wt% of camphorquinone and 1.03 wt% of benzoyl peroxide. This monomer liquid was incorporated with aldehyde as shown in Table 6 to make compositions. The resulting compositions were examined for curing time in the same way as in Example 1. The results are shown in Table 6.

TABLE 6

| No. | Monomer liquid containing quinone & BPO (mg) | Aldehyde | Amount (mg) | Curing time (sec) |
| --- | --- | --- | --- | --- |
| 1 | 237.2 | — | — | 70 |
| 2 | 219.3 | p-Tolualdehyde | 4.2 | 28 |
| 3 | 217.7 | Lauraldehyde | 5.4 | 18 |
| 4 | 230.6 | 1,9-Nonanedial | 2.8 | 15 |
| 5 | 232.3 | p-Phthaldialdehdye | 4.8 | 28 |
| 6 | 235.6 | β-Naphthaldehyde | 1.9 | 42 |
| 7 | 226.3 | p-Cyanobenzaldyde | 3.8 | 42 |
| 8 | 245.5 | Citral | 4.5 | 33 |
| 9 | 228.0 | Citronellal | 3.0 | 20 |

EXAMPLE 7 AND COMPARATIVE EXAMPLE 5

The same monomer liquid as in Example 1 was incorporated with a photosensitizer as shown in Table 7. The monomer liquid was divided into two portions. One portion was irradiated with light without addition of aldehyde and the other was irradiated with light after addition of p-tolualdehyde. They were examined for curing time. Irradiation was carried out in the same way as in Example 1. The results are shown in Table 7.

TABLE 7

| No. | Photosensitizer, amount added (wt %) | Amount of monomer liquid (mg) | Amount of p-tolualdehyde added (mg) | Curing time (sec) |
| --- | --- | --- | --- | --- |
| 1* | β-Naphthoquinone (0.03) | 242.5 | — | 210 |
| 1 | β-Naphthoquinone (0.03) | 237.4 | 4.6 | 110 |
| 2* | Diacetyl (0.97) | 233.0 | — | 150 |
| 2 | Diacetyl (0.97) | 232.6 | 6.6 | 120 |
| 3* | 2,3-Heptanedione (1.09) | 234.9 | — | 240 |
| 3 | 2,3-Heptanedione (1.09) | 234.1 | 3.5 | 210 |
| 4* | Phenanthraquinone (0.05) | 237.0 | — | 130 |
| 4 | Phenanthraquinone (0.05) | 221.2 | 2.9 | 90 |

*Comparative examples.

EXAMPLE 8 AND COMPARATIVE EXAMPLE 6

Example 1 was repeated using the compositions shown in Table 8. The quantity of the composition was 220 to 230 mg.

TABLE 8

| | Monomer composition (parts by weight) | | Sensitizer and amount (parts by weight) | | Accelerator and amount (parts by weight) | | Curing time (min) | |
|---|---|---|---|---|---|---|---|---|
| 1* | Styrene | 25.8 | Camphorquinone | 0.99 | — | | 8 | (gelation) |
| | Pentaerythritol trimethacrylate | 74.2 | | | | | | |
| 1 | Styrene | 25.8 | Camphorquinone | 0.99 | Lauraldehyde | 2.5 | 2.5 | |
| | Pentaerythritol trimethacrylate | 74.2 | | | | | | |
| 2* | Epoxy ester (3002)+ | 33 | Camphorquinone | 0.99 | — | | 12< | (no cure) |
| | Trimethylolpropane trimethacrylate | 33 | | | | | | |
| | Methyl methacrylate | 33 | | | | | | |
| 2 | Epoxy ester (3002)+ | 33 | Camphorquinone | 0.99 | Lauraldehyde | 2.5 | 12 | |
| | Trimethylolpropane trimethacrylate | 33 | | | | | | |
| | Methyl methacrylate | 33 | | | | | | |
| 3* | Styrene | 63 | Camphorquinone | 0.91 | — | | 10< | (no cure) |
| | bis-GMA | 37 | | | | | | |
| 3 | Styrene | 63 | Camphorquinone | 0.91 | Lauraldehyde | 2.5 | 9 | |
| | bis-GMA | 37 | | | | | | |
| 4* | Epoxy ester (3002) | 79 | Pentanedione | 1.62 | — | | 10< | (no cure) |
| | Methyl cinnamate | 21 | | | | | | |
| 4 | Epoxy ester (3002) | 79 | Pentanedione | 1.62 | p-Toluadehyde | 2.5 | 10 | |
| | Methyl cinnamate | 21 | | | | | | |
| 5* | Phenyl P monomer++ | 5 | Camphorquinone | 0.73 | — | | 7 | |
| | bis-GMA | 75 | | | | | | |
| | Triethyleneglycol dimethacrylate | 20 | | | | | | |
| 5 | Phenyl P monomer++ | 5 | Camphorquinone | 0.73 | Citral | 2.39 | 1.67 | |
| | bis-GMA | 75 | | | | | | |
| | Triethyleneglycol dimethacrylate | 20 | | | | | | |
| 6 | Phenyl P monomer++ | 5 | Camphorquinone | 0.73 | Citronellal | 2.01 | 0.75 | |
| | bis-GMA | 75 | | | | | | |
| | Triethyleneglycol dimethacrylate | 20 | | | | | | |

Note to Table 8.
*Comparative Examples.
+Structural formula:

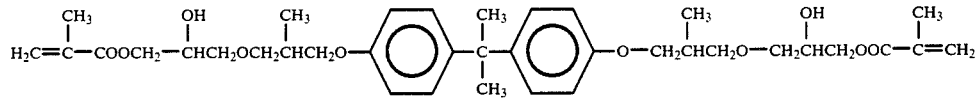

++Structural formula:

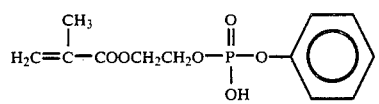

EXAMPLE 9 AND COMPARATIVE EXAMPLE 7

A photopolymerizable dental composite resin containing aldehyde was prepared according to the following formulation (Example 9).

| Formulation: | |
|---|---|
| Bis-GMA | 0.864 g |
| 3G | 0.288 g |
| Camphorquinone | 0.012 g |
| Benzoyl peroxide | 0.012 g |
| Lauraldehyde | 0.024 g |
| Silane-treated quartz powder | 3.871 g |
| Colloidal silica | 0.103 g |

These components were mixed in a mortar, and the resulting paste was degassed under vacuum. The paste sample was filled in a glass tube having an inside diameter of 4 mm, and was cured by irradiating with light emitted from a Translux (15V-150W halogen-tungsten lamp, made by Kulzer & Co., GMBH) placed 4 mm apart. The light was directed to one end of the glass tube. From the other end of the glass tube a needle, 1 mm in diameter, was thrusted into the cured composition. A load of 260 g was applied to this needle for 30 seconds to measure the degree of penetration. This value was used to calculate the thickness of the cured part. It was found that irradiation for 5 seconds and 10 seconds cured up to 11 mm and 20 mm, respectively.

In Comparative Example 7, the composition was prepared without lauraldehyde. The depth of cure by irradiation for 10 seconds was only 5 mm.

EXAMPLE 10

A photopolymerizable dental composite resin was prepared according to the following formulation. Formulation:

| Formulation: | |
|---|---|
| Bis-GMA | 1.00 g |
| 2,2'-di(4-methacryloxypolyethoxyphenyl)propane (2.6 ethoxy groups on average in one molecule) | 1.00 g |
| 3G | 0.828 g |

-continued

| Formulation: | |
|---|---|
| Camphorquinone | 4.6 mg |
| Benzoyl peroxide | 30.9 mg |
| p-Tolualdehyde | 85 mg |
| Titanium dioxide | 3.0 mg |
| Iron oxide red | 50 µg |
| Iron oxide yellow | 100 µg |
| Carbon black | 5 µg |
| Silane-treated quartz powder | 9.90 g |
| Colloidal silica | 0.25 g |

These components were mixed in a mortar to give a paste and the cure depth was measured in the same way as in Example 9. The cure depths of 6.3 mm and 10.2 mm were accomplished with irradiation for 20 seconds and 60 seconds, respectively.

COMPARATIVE EXAMPLE 8

A photopolymerizable composition was prepared according to the following formulation.

| Formulation: | |
|---|---|
| Bis-GMA | 0.722 g |
| 3G | 0.309 g |
| Benzil | 0.02 g |
| Dimethylamino-benzaldehyde | 0.019 g |
| Silane-treated quartz powder | 3.379 g |
| Colloidal silica | 0.102 g |

These components were mixed in a mortar to give a paste and the cure depth was measured in the same way as in Example 9. A cure depth of 4.5 mm was achieved with irradiation for 20 seconds; but the cured product was severely colored yellow. It was apparently unsuitable for dental use. It is considered that this discoloration is due to dimethylaminobenzaldehyde used as a polymerization initiator.

In the meantime, no discolorization was observed in the cured resin compositions in Examples 9 and 10.

EXAMPLE 11 AND COMPARATIVE EXAMPLE 9

Photopolymerizable compositions were prepared according to the formulations shown in Table 9. They were examined for storage stability. The results are shown in Table 10.

TABLE 9

| Component | Experiment No. | | | | |
|---|---|---|---|---|---|
| | 1* | 2* | 3* | 1 | 2 |
| Bis-GMA (g)** | 0.7 | 0.7 | 0.7 | 0.7 | 0.7 |
| 3G (g)** | 0.3 | 0.3 | 0.3 | 0.3 | 0.3 |
| Camphorquinone (g) | 0.005 | 0.005 | 0.005 | 0.005 | 0.005 |
| Accelerator (g) | | | | | |
| N,N—dimethylamino-benzaldehyde | 0.02 | 0.02 | — | — | — |
| N,N—dimethylamino-ethyl methacrylate | — | — | 0.02 | — | — |
| Terephthalaldehyde | — | — | — | 0.025 | 0.025 |
| BPO (g) | — | 0.01 | 0.01 | — | 0.01 |
| Silane-treated quartz powder (g) | 3.40 | 3.40 | 3.40 | 3.40 | 3.40 |
| Colloidal silica (g) | 0.10 | 0.10 | 0.10 | 0.10 | 0.10 |

*Comparative Examples
**Contains 500 ppm of 2,6-di-t-butyl-4-methylphenol.

TABLE 10

| No. | Number of days required for the composition to solidify at 50° C. (days) | Number of days required for the composition to solidify at room temperature (days) |
|---|---|---|
| 1* | 14 | 60 |
| 2* | — | Solidified during preparation |
| 3* | 12 | 60 |
| 1 | >30 | >600 |
| 2 | 26 | >600 |

*Comparative Examples

It is to be noted from the above table that the composition of this invention is superior in storage stability.

EXAMPLE 12 AND COMPARATIVE EXAMPLE 10

Dental composited resins were prepared according to the following formulations.

| Formulation 1: | |
|---|---|
| 2,2'-di-(4-methacryloxy-polyethoxyphenyl)propane (having 2.6 ethoxy groups on average in one molecule) | 2.1 g |
| 3G | 0.9 g |
| Camphorquinone | 0.015 g |
| Benzoyl peroxide | 0.06 g |
| Tetradecyl aldehyde | 0.09 g |
| Silane-treated quartz powder | 11.7 g |
| Colloidal silica | 0.46 g |
| Iron oxide red | 50 µg |
| Iron oxide yellow | 100 µg |
| Titanium dioxide | 3 mg |
| Formulation 2: | |
| Bis-GMA | 2.1 g |
| 3G | 0.9 g |
| Camphorquinone | 0.015 g |
| Benzoyl peroxide | 0.06 g |
| 3,4-Diethoxybenzaldehyde | 0.09 g |
| Silane-treated quartz powder | 11.7 g |
| Colloidal silica | 0.46 g |
| Iron oxide red | 50 µg |
| Iron oxide yellow | 100 µg |
| Titanium dioxide | 3 mg |
| Formulation 3: | |
| Bis-GMA | 2.1 g |
| 3G | 0.9 g |
| Camphorquinone | 0.015 g |
| Benzoyl peroxide | 0.06 g |
| p-n-Octyloxybenzaldehyde | 0.09 g |
| Silane-treated quartz powder | 11.7 g |
| Colloidal silica | 0.46 g |
| Iron oxide red | 50 µg |
| Iron oxide yellow | 100 µg |
| Titanium dioxide | 3 mg |
| Formulation 4: (Comparative) | |
| Bis-GMA | 2.1 g |
| 3G | 0.9 g |
| Camphorquinone | 0.015 g |
| N,N—dimethylaminoethyl methacrylate | 0.03 g |
| Silane-treated quartz powder | 11.7 g |
| Colloidal silica | 0.46 g |
| Iron oxide red | 50 µg |
| Iron oxide yellow | 100 µg |
| Titanium dioxide | 3 mg |
| Formulation 5: (Comparative) | |
| Bis-GMA | 2.1 g |
| 3G | 0.9 g |
| Camphorquinone | 0.015 g |
| N,N—dimethylaminoethyl methacrylate | 0.03 g |
| Benzoyl peroxide | 0.06 g |
| Silane-treated quartz powder | 11.7 g |
| Colloidal silica | 0.46 g |
| Iron oxide red | 50 µg |
| Iron oxide yellow | 100 µg |

| | |
|---|---|
| -continued | |
| Titanium dioxide | 3 mg |

The components of each formulation were mixed in a mortar and the resulting paste was degassed under vacuum. The thus prepared compositions were tested as follows: (A) Each composition in the form of paste prepared as mentioned above was filled into a cylindrical cavity, 4 mm in diameter and 3 mm deep, formed on the occusal surface of a human molar. Prior to filling, the cavity was treated with 40% phosphoric acid and then a bonding agent ("Clearfil New Bond) containing a phosphate ester monomer. The filled paste was irradiated for 40 seconds with light emitted from Translux. After curing, the sample molar was dipped in water at 37° C. for 24 hours. Excess resin was ground off. The sample molar was dipped in cold water (4° C.) and hot water (60° C.) for 1 minute each alternatively. The dipping was repeated 100 times. Finally, the sample molar was dyed with 0.1% aqueous solution of basic fuchsin. There was no sign of fuchsin entering to the tooth cavities in formulations 1 to 3. But there was a little in formulations 4 to 5. (B) The composition was examined for adhesive strength. The bovine anterior labial surface was polished with emery paper to make a smooth enamel surface. A piece of adhesive tape having a hole, 5 mm in diameter, was attached to the smooth enamel surface to establish the bonding area. The enamel surface was treated with 40% phosphoric acid for 45 seconds (acid etching) and then a commercial bonding agent ("Clearfil New Bond") was applied to the etched surface. The paste prepared as mentioned above was placed on the treated enamel surface and spread over it with a piece of glass. The paste was cured by irradiating for 40 seconds with light emitted from Translux. After curing, the glass was removed. A stainless steel round rod (7 mm in diameter) was bonded vertically to the cured resin with a commercial adhesive filling material ("Clearfil F II"). The assembly was dipped in water at 37 overnight. The adhesive strength was measured by using an Instron TT-B universal materials testing machine. The above-mentioned test was also conducted for the human tooth dentin. The results are shown in Table 11.

TABLE 11

| | Bovine enamel (kg/cm$^2$) | Human dentin (kg/cm$^2$) |
|---|---|---|
| Example 12 | | |
| Formulation 1 | 170 | 140 |
| Formulation 2 | 170 | 130 |
| Formulation 3 | 160 | 130 |
| Comparative Example 10 | | |
| Formulation 4 | 92 | 80 |
| Formulation 5 | 130 | 95 |

(C) The composition was examined for compressive strength. The paste prepared as mentioned above was filled in a stainless less steel cylindrical mold, 4 mm high and 4 mm in diameter, and compacted by glass plates at both ends of the mold. The paste filled in the mold was irradiated for one minute with Translux each for top and bottom. After curing, the assembly was kept in a constant temperature air bath at 37° C. for 24 hours. The cured sample was removed from the mold, and the compressive strength of the sample was measured by using an Instron tester.

On the other hand, the paste prepared as mentioned above was filled in a stainless steel cylindrical mold, 3 mm high and 6 mm in diameter, and cured in the same way as mentioned above. The cured sample was removed from the mold and dipped in water at 37° C. for 24 hours. The diametral tensile strength of the sample was measured by using an Instron tester. The results are shown in Table 12.

TABLE 12

| | Compressive strength (kg/cm$^2$) | Diametral tensile strength (kg/cm$^2$) |
|---|---|---|
| Example 12 | | |
| Formulation 1 | 3500 | 580 |
| Formulation 2 | 3400 | 600 |
| Formulation 3 | 3450 | 610 |
| Comparative Example 10 | | |
| Formulation 4 | 2820 | 530 |
| Formulation 5 | 3090 | 530 |

(D) The compositions were examined for storage stability as follows: The pastes of Formulation 2 and Formulation 5 (Comparative Example) were stored in a constant temperature air bath at 45° C. At regular intervals, the samples were examined for compressive strength, diametral tensile strength, and cure depth to see the change in performance with time. The samples for compressive strength and diametral tensile strength were irradiated for 1 minute with Translux as shown in Example 12(C) and the samples for cure depth were irradiated for 20 seconds. The results are shown in Table 13.

TABLE 13

| | Period of storage (days) | | | | |
|---|---|---|---|---|---|
| | 0 | 3 | 7 | 14 | 21 |
| Formulation 2 | | | | | |
| Compressive strength (kg/cm$^2$) | 3400 | 3460 | 3475 | 3520 | 3460 |
| Tensile strength (kg/cm$^2$) | 600 | 632 | 649 | 648 | 640 |
| Depth of cure (mm) | 5.00 | 4.81 | 4.67 | 5.04 | 5.14 |
| Formulation 5* | | | | | |
| Compressive strength (kg/cm$^2$) | 3090 | 3120 | 3130 | 2920 | 3150 |
| Tensile strength (kg/cm$^2$) | 530 | 545 | 470 | 540 | 540 |
| Depth of cure (mm) | 5.10 | 4.63 | 3.93 | 3.85 | 3.49 |

*The samples were tinged with red under the above storage conditions.

What is claimed is:

1. A photopolymerizable composition, which comprises a polymerizable monomer and an initiator capable of polymerizing said monomer upon exposure to visible light, wherein said initiator comprises (a) at least one kind of photosensitizer selected from α-diketone compounds, (b) at least one kind of accelerator selected from an aldehyde containing no amino groups, and (c) an organic peroxide.

2. A photopolymerizable composition as set forth in claim 1, wherein the α-diketone compounds are represented by the following formula:

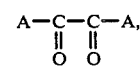

where A denotes an aliphatic hydrocarbon group of 1 to 20 carbon atoms, wherein two of A may be the same or different, and wherein two of A may bond to each other to form a cyclic structure.

3. A photpolymerizable composition as set forth in claim 2, wherein the photosensitizer is camphorquinone, diacetyl, 2,3-pentanedione, 2,3- or 3,4-hexanedione, or 2,3-, 3,4-, or 4,5-octanedione.

4. A photopolymerizable composition as set forth in claim 2, wherein the aldehyde is a compound represented by the formula B(CHO)$_n$, where B denotes an acyclic or alicyclic saturated or unsaturated aliphatic hydrocarbon group of 1 to 20 carbon atoms or a monocyclic or polycyclic aromatic hydrocarbon group of 1 to 20 carbon atoms, wherein the hydrocarbon group may have a substituent group of 1 to 20 carbon atoms, and n is an integer of 1 to 3.

5. A photopolymerizable composition as set forth in claim 4, wherein the aldehyde is alkylmonoaldehyde or alkyldialdehyde of 1 to 20 carbon atoms, polyalkyl ether mono- or dialdehyde of 1 to 20 carbon atoms, or a compound represented by the formula

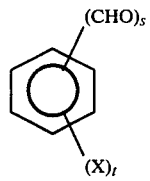

where s is 1 or 2; X denotes an alkyl, alkoxy, or polyalkylether of 1 to 20 carbon atoms; and t is an integer of 0 to 3.

6. A photopolymerizable composition as set forth in claim 1, wherein the organic peroxide is a diacyl peroxide or peroxy ester.

7. A photopolymerizable composition as set forth in claim 6, wherein the organic peroxide is benzoyl peroxide, t-butyl perbenzoate, di-t-butyl peroxyisophthalate, or 2,5-dimethyl-2,5-di(benzoylperoxy)hexane.

8. The photopolymerizable composition as set forth in claim 1, which further comprises a filler.

9. A photopolymerizable composition for use in dental applications, which comprises a photopolymerizable monomer; an initiator capable of polymerizing said monomer upon exposure to visible light, wherein said initiator comprises (a) at least one kind of photosensitizer selected from α-diketone compounds (b) at least one kind of accelerator selected from an aldehyde containing no amino groups, and (c) an organic peroxide; and from about 20–90% by weight of a filler.

10. The composition of claim 9, wherein said photopolymerizable monomer is contained in an amount of from about 80 to 10% by weight.

* * * * *